(12) United States Patent
Patel

(10) Patent No.: US 11,844,778 B2
(45) Date of Patent: Dec. 19, 2023

(54) LUTEOLIN FOR TREATMENT OF NEUROMUSCULAR MOVEMENT DISORDER

(71) Applicant: UNIVERSITY OF SOUTH CAROLINA, Columbia, SC (US)

(72) Inventor: Rekha Patel, Irmo, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 17/883,227

(22) Filed: Aug. 8, 2022

(65) Prior Publication Data

US 2023/0233512 A1    Jul. 27, 2023

Related U.S. Application Data

(60) Provisional application No. 63/253,699, filed on Oct. 8, 2021.

(51) Int. Cl.
*A61K 31/352* (2006.01)
*A61P 25/14* (2006.01)

(52) U.S. Cl.
CPC ............ *A61K 31/352* (2013.01); *A61P 25/14* (2018.01)

(58) Field of Classification Search
CPC .............................. A61K 31/352; A61P 25/14
See application file for complete search history.

(56) References Cited

PUBLICATIONS

Burnett et al. A truncated PACT protein resulting from a frameshift mutation reported in movement disorder DYT16 triggers caspase activation and apoptosis. Journal of Cellular Biochemistry, vol. 120, 19004-19018. (Year: 2019).*
Burnett et al., Dystonia 16 (DYT16) Mutations in PACT Cause Dysregulated PKR Activation and eIF2α Signaling Leading to a Compromised Stress Response, Neurobiology of Disease, vol. 146, 2020, 105135. https://doi.org/10.1016/j.nbd.2020.105135.

* cited by examiner

*Primary Examiner* — Sikarl A Witherspoon
(74) *Attorney, Agent, or Firm* — DORITY & MANNING, P.A.

(57) ABSTRACT

Methods for modification of abnormal protein interactions manifested as excessive PACT-mediated PKR activation within cells are described. Methods include administration of luteolin to cells that exhibit dysregulation in PACT-mediated PKR activation. Methods can decrease or prevent excessive non-viral PACT-mediated PKR activation in a cell as may occur due to expression by the cell of a mutant PACT protein. Methods can decrease an abnormal prolonged stress response as may occur in the absence of a stress-inducing activity or agent.

19 Claims, 9 Drawing Sheets
Specification includes a Sequence Listing.

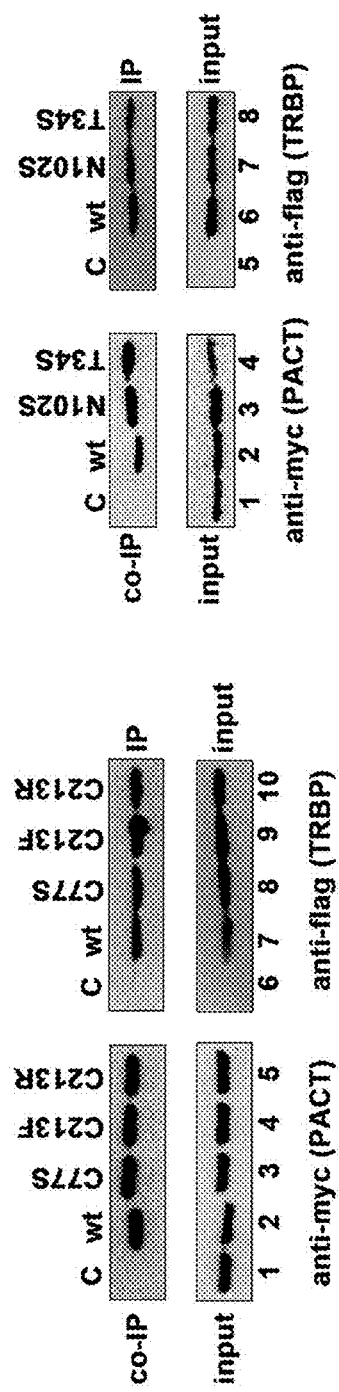
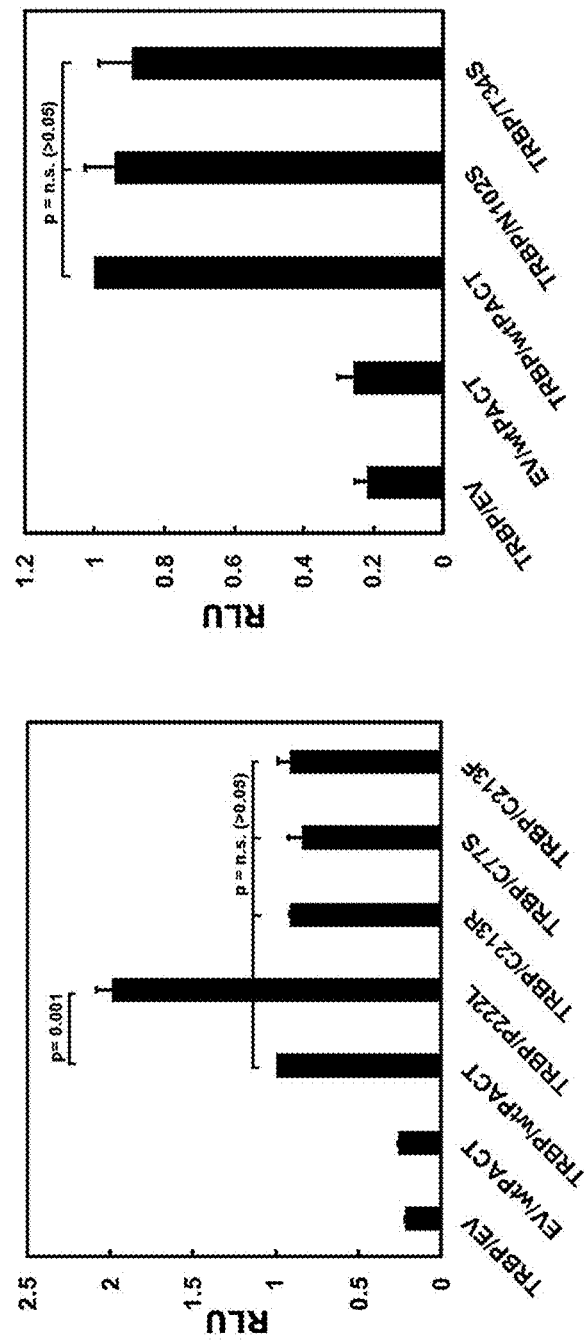
FIG. 6A
FIG. 6B
FIG. 6C
FIG. 6D

LUTEOLIN FOR TREATMENT OF NEUROMUSCULAR MOVEMENT DISORDER

CROSS REFERENCE TO RELATED APPLICATION

This application claims filing benefit of U.S. Provisional Patent Application Ser. No. 63/253,699, having a filing date of Oct. 8, 2021, which is incorporated herein by reference for all purposes.

STATEMENT REGARDING FEDERALLY SPONSORED RESEARCH OR DEVELOPMENT

This invention was made with government support under Grant No. W81XWH-18-1-0088, awarded by the US Department of Defense. The government has certain rights in the invention.

SEQUENCE LISTING

The instant application contains a Sequence Listing which has been submitted electronically in XML file format and is hereby incorporated by reference in its entirety. Said XML copy, created on Mar. 24, 2023, is named USC-705_SL.xml and is 10,900 bytes in size.

BACKGROUND

Dystonia 16 (DYT16) is one of a group of disorders generally referred to as dystonias. Dystonias are a heterogeneous group of movement disorders in which the effected individuals exhibit repetitive and painful movements of the affected limbs, as well as compromised posture and gait pattern. DYT16 is a rare, early-onset dystonia parkinsonism disorder characterized by progressive limb dystonia, laryngeal and oromandibular dystonia, and parkinsonism. Recently, eight different mutations have been identified in the Prkra gene, encoding PACT (OMIM: DYT16, 612067), in patients diagnosed with DYT16. PACT is the protein activator of interferon-induced double stranded RNA-activated protein kinase (PKR).

Activated PKR regulates the integrated stress response (ISR) via phosphorylation of the translation initiation factor eIF2α. PKR activation and resulting EIF2α phosphorylation is the central event in the ISR, which is an evolutionarily conserved pathway activated in eukaryotic cells by many different types of stress stimuli in order to restore cellular homeostasis. Once triggered, the ISR attenuates general protein synthesis while concomitantly triggering enhanced translation of a few specific transcripts leading either to recovery and homeostasis or cellular apoptosis, depending on the intensity and duration of stress signals. In virally infected cells, PKR is activated by direct interactions with dsRNA, which is a viral replication intermediate for many viruses. In the absence of viral infection, other stress signals activate PKR via PACT in a dsRNA-independent manner. Thus, PACT is a stress-modulated activator of PKR that works via a direct, dsRNA-independent interaction in response to cellular stress conditions, including endoplasmic reticulum (ER) stress, oxidative stress, and serum deprivation.

In the absence of stress, both PACT and PKR are bound by their inhibitor, transactivation RNA-binding protein (TRBP), thereby keeping PKR inactive. Under conditions of cellular stress, these inhibitory interactions dissociate facilitating PACT-PACT homomeric interactions, thereby enabling PACT-PKR interaction that activates PKR, resulting in EIF2α phosphorylation and subsequent ISR events. Upon recovery, PACT-PKR and PACT-PACT dimers dissociate and are again bound by their TRBP inhibitors. When PKR activation is transient, it helps the cells recover from stress, but when PKR activation is prolonged, cells cannot recover and undergo apoptosis.

Previous studies have shown that PACT mutations present in DYT16 can increase cell susceptibility to ER stress and that PACT frameshift mutation in DYT16, as well as in other dystopias, can lead to disruption in formation of PACT-TRBP heterodimers, increasing PACT-mediated PKR activation.

Needed in the art are further understandings of excessive of PACT-mediated PKR activation that occurs in dystonias as well as in other diseases. Also needed in the art are materials and methods developed in light of these understandings that can be used to modify or prevent this dysregulation and provide therapeutic options in treatments for dystonias as well as other conditions that include excessive PACT-mediated PKR activation.

SUMMARY

According to one embodiment, disclosed is a method for disrupting non-viral PACT-mediated PKR activation in a cell. The method can include administering luteolin to a cell that exhibits a dysregulation in PACT-mediated PKR activation. For instance, the cell can express a PACT protein that includes one or more-point mutations as compared to a wild type PACT protein, and this point mutation can encourage excessive PACT-mediated PKR activation within the cell. Following the administration, interaction between PACT protein and PKR protein expressed by the cell can be decreased as compared to prior to the administration. For instance, the decrease can be indicated by one or more of a decrease in concentration or rate of formation of a PACT-PKR heterodimer by the cell following the administration, a decrease in concentration or rate of formation of a PACT-PACT homodimer by the cell following the administration, and an increase in concentration or rate of formation of a PACT-TBRP heterodimer by the cell following the administration.

According to one embodiment, disclosed is a method for decreasing an abnormal stress response in a cell, for instance, an abnormal stress response that is sustained in the absence of any stress inducing agent. The method can include administering luteolin to a cell. Following the administration, a stress response of the cell can decrease, e.g., expression or activity of a stress biomarker expressed by the cell can decrease following the administration to a level that indicates rescue of the cell from ISR, e.g., within about 10% of a normal, non-stress level for the biomarker.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 6A provides co-immunoprecipitation results showing the effect of recessive DYT16 mutations on PACT-TRBP interactions.

FIG. 6B provides co-immunoprecipitation results showing the effect of dominant DYT16 mutations on PACT-TRBP interactions.

FIG. 6C provides results of a mammalian two-hybrid assay showing the effect of recessive DYT16 mutations on PACT-TRBP interactions.

FIG. 6D provides results of a mammalian two-hybrid assay showing the effect of recessive DYT16 mutations on PACT-TRBP interactions.

Figure 1A:
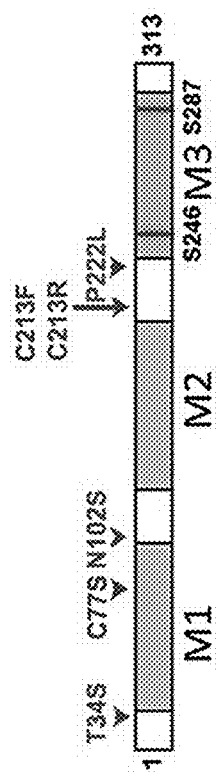
FIG. 1A provides a schematic representation of DYT16 mutations.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment may be used in another embodiment to yield a still further embodiment.

In general, the present disclosure is directed to methods for modification of abnormal protein interactions manifested as excessive PACT-mediated PKR activation within cells. Disclosed methods include administration of luteolin to cells that exhibit dysregulation in PACT-mediated PKR activation. Luteolin (3',4',5,7-tetrahydroxyflavone), is a flavonoid that exists in many types of plants, including fruits, vegetables, and medicinal herbs. In one embodiment, disclosed methods can decrease or prevent excessive non-viral, PACT-mediated PKR activation in a cell as may occur due to expression by the cell of a mutant PACT protein. In one embodiment, disclosed methods can be utilized to decrease a stress response, and in particular, an abnormal prolonged stress response as may occur in the absence of a stress-inducing activity or agent and that instead is an effect of a dysregulated PACT-mediated PKR activation within the cell.

The present invention has been developed from the realization that luteolin can interrupt pathological PKR activation by disrupting abnormal PACT interactions and preventing PKR-activating heterodimer formation between PACT and PKR in disease states. Additionally, the inventors have discovered that point mutations present in PACT in disease states can lead to excessive PKR activation via an increase in PACT-PACT interactions and/or an increase in PACT-PKR interactions, resulting in a mutant PACT-induced overactive ISR in the effected individual and leading to cellular apoptosis and related cellular and system damage.

Disclosed methods can be beneficially utilized in one embodiment in therapeutic application for conditions that include PACT mutation, including dystonias, e.g., DYT16. FIG. 1A presents a schematic representation of particular DYT16 mutations encompassed herein. As indicated in FIG. 1A, the majority of these DYT16 mutations occur outside of PACT's highly conserved double-stranded RNA binding motifs (dsRBMs), labeled as M1, M2, and M3 in the figure. The third dsRBM, M3, lacks dsRNA binding and includes two phosphorylation sites, represented as dark lines in FIG. 1A. Dominant DYT16 mutations include T34S and N102S, and recessive mutations include C77S, C213F, C213R, and P222L. The four mutations associated with the recessively inherited DYT16 (C77S, C213F, C213R, and P222L) result in the loss of a cysteine or proline residues which could have dramatical consequences on the 3-dimensional conformation of the protein. The two dominantly inherited mutations (N102S and T34S) occur on flanking ends of PACT's first dsRBM that is involved in dsRNA binding and protein-protein interactions.

However, it should be understood that disclosed methods are not limited to modification of PKR activation and/or ISR reduction as may be present in DYT16 affected cells/individuals only and may be utilized in conjunction with other dystonias, as well as other pathologies, that include dysregulation of PACT-mediated PKR activation, as the PACT-PKR stress response pathway functions ubiquitously in all cell types including neurons.

Individuals that have experienced traumatic brain or spinal cord injuries have been known to develop dystonia years after the initial injury (injury-induced dystonia). Similarly, individuals taking antipsychotic drugs for anxiety, post-traumatic stress disorder (PTSD), depression, etc. have been known to develop dystonia as a side effect (drug-induced dystonia). Disclosed methods may provide therapeutic benefit in such cases of induced dystonia, as well as congenital dystonias. For instance, as antipsychotic drugs have been known to induce PKR activation, disclosed methods may be beneficial in conjunction with antipsychotic therapy in prevention of drug-induced dystonia.

Embodiments of disease states encompassed herein can include diseases that include a PACT mutation, including congenital as well as induced mutations. For instance, a system encompassed herein (including cellular in vitro and ex vivo systems as well as in vivo systems in a therapeutic application) can exhibit one or more mutations in an expressed PACT that manifests in excessive PACT-PACT interaction (e.g., homodimer formation) and/or excessive PACT-PKR interaction (e.g., heterodimer formation) as compared to wild type (wt) PACT. In one embodiment, a PACT mutation encompassed herein can include one or more of a cysteine to serine mutation, a cysteine to phenylalanine mutation, a cysteine to arginine mutation, a proline to leucine mutation, threonine to serine mutation, and an asparagine to serine mutation.

PACT-mediated PKR activation and its involvement in neurodegeneration has been noted in Alzheimer's patients and mouse models. Overactivation of the normal PKR activation system has been implicated in several neurodegenerative diseases, in addition to Alzheimer's disease. For instance, increased levels of PKR phosphorylation have been detected in the brains of patients with neurodegenerative diseases including Alzheimer's disease, Parkinson's disease, Huntington's disease, dementia, and prion disease. Excessively activated PKR has also been shown to be responsible for behavioral and neurophysiological abnormalities in a mouse model of Down syndrome, and PKR inhibitory drugs partially rescued the synaptic plasticity and long-term memory deficits in mice.

Accordingly, disclosed methods can be utilized in modification of excessive PACT-mediated PKR activation and related ISR as may be present in individuals affected with congenital or induced dystonias as well as other disease states including, without limitation, Alzheimer's disease, Parkinson's disease, Huntington's disease, dementia, prion disease, and Down's Syndrome.

Disclosed methods may be particularly beneficial in therapeutic applications as many known PKR inhibitors such as C16 have been documented to have off target effects, thereby questioning its suitability in treatment of diseases such as DYT16, particularly when considered for long-term treatment. Luteolin has been examined previously for other uses, such as providing anti-inflammatory and antioxidant benefits, and has been shown to exhibit few or no significant side effects and is available without prescription. As described further in the Examples section, below, the beneficial effects of luteolin can take longer to manifest in affected cells as compared to effects seen in normal wt cells, and as such, therapeutic use of luteolin can provide benefit in long-term therapies, not only in direct benefit due to modification of excessive PACT-mediated PKR activation as described, but also in indirect benefit due to less concern of off-target side effects.

Through disruption of an excessive PACT-mediated PKR activation, disclosed methods can provide a route for decreasing an abnormal ISR and preventing long-term systemic damage resulting from the abnormal ISR. An ISR encompassed herein can encompass any non-viral stress response, including ER stress, oxidative stress, serum deprivation, etc.

A decrease in abnormal ISR can be determined by examination of concentration or rate of expression of a stress biomarker that can either increase or decrease in expression level upon rescue of a stress response, depending upon the particular biomarker examined. By way of example, and without limitation, ER stress biomarkers as may be utilized to determine a state of abnormal and/or rescued ISR can include determination of accumulation of misfolded proteins in the ER due to inhibition of protein glycosylation, anti-cleaved PARP1 and anti-β-actin antibodies, binding immunoglobulin protein (BiP), phosphorylated Inositol Requiring 1 protein (p-IRE), phosphorylated PKR-like ER kinase (p-PERK), and C/EBP homologous protein (CHOP).

Determination of success in rescuing cells from an abnormal ISR can include examination of the level of one or more stress biomarkers following administration of luteolin to the cells and recognition that the stress biomarker level has been modified so as to be at or near the normal, non-stress level for the biomarker, e.g., within about 10% of a normal, non-stress level for the biomarker.

Disclosed methods can be utilized in vivo for treatment of dysregulated PKR activation or in vitro or ex vivo for study of pathogenic cells or tissue. In order for disclosed materials to be effectively utilized in a clinical therapy, luteolin can be delivered so as to be provided with suitable bioavailability. It will be understood that the in vivo and ex vivo methods have application for both human and veterinary use.

The appropriate dosage ("therapeutically effective amount") of the luteolin can depend, for example, on the particular disease being treated, whether the luteolin is administered for therapeutic purposes or in prevention of side effects of another drug, e.g., an antipsychotic, previous therapy, the patient's clinical history and response to the luteolin, and the discretion of the attending physician, among other factors. Luteolin can be administered to a subject at one time or over a series of treatments and may be administered to the subject at any time.

In one embodiment, a therapeutically effective amount of luteolin can be in the range of about 0.001 mg/kg body weight/day to about 100 mg/kg body weight/day, whether by one or more administrations, for instance, at a concentration of from about 1 mg/mL to about 50 mg/mL. For example, luteolin can be administered in an amount of from about 1 mg/kg body weight per day to about 50 mg/kg body weight/day, in some embodiments. For instance, luteolin can be provided to the targeted site, e.g., cells that carry a mutant PACT, such that the luteolin is at a concentration of about 10 micromolar (10 μM) or greater at the site of contact, for instance, at a concentration of from about 10 μM to about 100 μM, or about 50 μM, in some embodiments. As expected, the dosage can be dependent on the condition, size, age, and condition of the patient.

Luteolin may be administered, as appropriate or indicated, in a single oral dose or as multiple oral doses. Multiple doses may be administered, for example, multiple times per day, once daily, multiple times per week, every 2, 3, 4, 5, 6 or 7 days, weekly, every 2, 3, 4, 5 or 6 weeks or monthly. However, other dosage regimens may be useful. The progress of this therapy is easily monitored by conventional techniques.

It can be advantageous to formulate oral compositions in dosage unit form for ease of administration and uniformity of dosage. Dosage unit form as used herein includes physically discrete units suited as unitary dosages for the subject to be treated; each unit may contain a predetermined quantity of active compound calculated to produce the desired therapeutic effect in association with the required pharmaceutical carrier. The specification for the dosage unit forms of the application is dictated by and directly dependent on the unique characteristics of the active compound and the particular therapeutic effect to be achieved, and the limitations inherent in the art of compounding such an active compound for the treatment of individuals.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules.

Pharmaceutically compatible binding agents and/or adjuvant materials can be included as part of an orally ingestible composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

When administered orally in liquid form, a liquid carrier such as oils of animal or plant origin such as peanut oil, olive oil, mineral oil, soybean oil, or sesame oil, or synthetic oils may be added. A liquid form may further contain physiological dextrose or other saccharide solution, or glycols such as ethylene glycol, propylene glycol or polyethylene glycol. When administered in liquid form, a composition can contain from about 0.5 to 90% by weight luteolin, in one embodiment, from about 1 to 50% by weight luteolin.

In certain embodiments, a pharmaceutical composition can be formulated for sustained or controlled release of luteolin. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to specific cells with monoclonal antibodies to viral antigens) can also be used as pharmaceutically acceptable carriers. These can be prepared according to methods known to those skilled in the art. For instance, in some embodiments, luteolin can be complexed in the form of nanoparticles, which can improve aqueous solubility of the luteolin and consequently, its bioavailability. By way of example, luteolin can be encapsulated using nanostructured lipid carriers or microemulsions. Polymeric nanoparticles as may be formed to encapsulate luteolin (e.g., through precipitation of particles in the presence of luteolin or other known formation techniques) can include, without limitation, polyethylene glycol (PEG), methoxy PEG—polylactide-co-glycolide (PEG-PLG), methoxy PEG—polylactide, methoxy PEG—polycaprolactone, polylactic acid (PLA)—PEG ether, etc., as well as combinations of polymers or copolymers. Such formulations can exhibit an improved therapeutic value in some embodiments.

The present disclosure may be better understood with reference to the Examples set forth below.

Example

Methods and Materials
Cell Lines and Antibodies

Both HeLaM and COS-1 cells were cultured using Dulbecco's Modified Eagle's Medium (DMEM) containing 10% Fetal Bovine Serum and penicillin/streptomycin. Wild type (wt) and DYT16 Patient B-Lymphoblasts were cultured in RPMI 1640 medium containing 10% FBS and penicillin/streptomycin. Both wt and DYT16 patient lymphoblast cell lines were Epstein-Barr Virus-transformed to create stable cell lines. All transfections were carried using Effectene® transfection reagent (Qiagen) per manufacturer protocol. The antibodies used were as follows:

PKR: Anti-PKR (human) monoclonal (71/10, R&D Systems),
P-PKR: Antiphospho-PKR (Thr-446) monoclonal (Abcam, [E120]),
eIF2α: AntieIF2α polyclonal (Invitrogen™, AHO1182),
p-eIF2α: Anti-phospho-eIF2α (Ser-51) polyclonal (CST, #9721),
PACT: Anti-PACT monoclonal (Abcam, ab75749),
ATF4: Anti-ATF4 monoclonal (CST, #11815),
CHOP: Anti-CHOP monoclonal (CST, #2895),
Cleaved PARP: Anti-Cleaved-PARP monoclonal (CST, #32563),
FLAG-HRP: Anti-FLAG monoclonal M2-HRP (Sigma® A8592),
MYC-HRP: Anti-MYC monoclonal (Santa Cruz, 9E10),
β-Actin: Anti-β-Actin-Peroxidase monoclonal (Sigma-Aldrich™, A3854).

Generation of DYT16 Point Mutations

Each DYT16 mutant construct was generated using site specific mutagenesis through PCR amplification changing the codon within the PRKRA gene to be consistent with DYT16 patients and code for the appropriate amino acid substitution. The following site-specific mutagenic primer pairs were used:

```
C77S Sense:
                                        (SEQ ID NO: 1)
5'-GCT CTA GAC ATA TGG AAA TGT CCC AGA GCA

GGC AC-3'

C77S Antisense:
                                        (SEQ ID NO: 2)
5'-GCC TCT GCA GCT CTA TGT TTC GCC AGC TTC

TTA CTT GTA CCT TCA CCT GTG GAG GTT ATG TCA

CCA ACG G-3'

C213F Sense:
                                        (SEQ ID NO: 3)
5'-GCT CTA GAC ATA TGG AAA TGT CCC AGA GCA

GGC AC-3'
```

-continued

C213F Antisense:
(SEQ ID NO: 4)
5'-GGA GAA TTC CTC AAG GAA TGC CAA GTA

AAT CCT AAA GAA TGT CC-3'

C213R Sense:
(SEQ ID NO: 5)
5'-GCT CTA GAC ATA TGG AAA TGT CCC AGA

GCA GGC AC-3'

C213R Antisense:
(SEQ ID NO: 6)
5'-GGA GAA TTC CTC AAG GAA TGC CAA GTA

CGT CCT AAA GAA TGT CC-3'

N102S Sense:
(SEQ ID NO: 7)
5'-GCT GCA GAG GCT GCC ATA AAC ATT TTG

AAA GCC AGT GCA AGT ATT TGC

TTT GC-3'

N102S Antisense:
(SEQ ID NO: 8)
5'-GGG GAT CCT TAC TTT CTT TCT GCT

ATT ATC-3'

T34S Sense:
(SEQ ID NO: 9)
5'-GCT CTA GAC ATA TGG AAA TGT CCC

AGA GCA GGC AC-3'

T34S Antisense:
(SEQ ID NO: 10)
5'-CGT GTA ATA CCT GAA TCG GTG ATT

TCC CTG GCT TAG C-3'

To generate each construct, PCR amplification was performed to mutate the corresponding wt sequence to code for the amino acid residue consistent with the DYT16 patients. Each PCR product was then subcloned into pGEMT-easy vector (Promega®) and sequences were validated through DNA sequencing. After sequence validation, full length DYT16 ORFs were generated through cutting: (i) partial DYT16 ORF in pGEMT-easy with construct specific restriction enzymes, and (ii) Amino terminal FLAG or Myc-tagged wt PACT in BSIIKS+ with compatible restriction sites. Cloning scheme was as follows: C77S in pGEMT-easy cut with NdeI-PstI ligated into FLAG/Myc-PACT-BSIIKS+ cut with PstI-BamHI. C213F and C213R in pGEMT-easy cut with NdeI-EcoRI ligated into FLAG/Myc-PACT-BSIIKS+ cut with EcoRIBamHI. N102S in pGEMT-easy cut with NdeI-PstI and ligated into FLAG/Myc-PACT-BSIIKS+ cut with PstI-BamH1. T34S in pGEMT-easy cut with NdeI-TfiI ligated into FLAG/Myc-PACT-BSIIKS+ cut with TfiIBamHI. Once full length DYT16 ORFs were generated with amino terminal FLAG or Myc tags each ORF was then subcloned into pCDNA3.1– using XbaI-BamHI restriction sites. All DYT16 constructs were also cloned into Mammalian two-hybrid system vectors and pET15b (Novagen) using NdeI-BamHI restriction sites. TRBP and Flag-PKR constructs as known were utilized.

Expression and Purification of PACT from *E. coli*

The ORFs of both wt PACT and all DYT16 point mutations were subcloned into pET15b (Novagen®) to generate an in-frame fusion protein with a histidine tag. Recombinant proteins were then expressed and purified according to standard practice.

dsRNA Binding Assays

Both wt PACT and DYT16 PACT constructs in pCDNA3.1– were in vitro translated using the TNT-T7-coupled rabbit reticulocyte system from Promega® while incorporating an 35S-methionine radiolabel and the dsRNA binding ability was measured using poly(I:C) conjugated agarose beads. 4 µL of in vitro translation was diluted in 25 µL of binding buffer (20 mM Tris-HCl, pH 7.5, 0.3 M NaCl, 5 mM MgCl2, 1 mM DTT, 0.1 mM PMSF, 0.5% NP-40, 10% glycerol) and incubated in 25 µL of poly(I:C)-agarose beads and incubated at 30° C. for 30 minutes. The beads were then washed 4 times with 500 µL of binding buffer and bound proteins were analyzed via SDS-PAGE gel electrophoresis and autoradiography. The competition assay was performed incubating either soluble single-stranded RNA, poly(C), or dsRNA, poly(I:C), with the poly(I:C)-agarose beads before the adding the in vitro translated proteins. To ensure the presence of PACT was due to the dsRNA binding capacity in vitro translated 35S-methionine labeled firefly luciferase which has no dsRNA binding ability was assayed. Bands in bound and total lanes were quantified using Typhoon™ FLA7000 by analyzing relative band intensities of both T and B lanes. Percentage of PACT bound to beads was calculated and plotted as bar graphs.

PKR Activity Assays

HeLa M cells were treated with IFN-β for 24 hours and harvested at 70% confluency, washed using ice-cold PBS and centrifuged at 600 g for 5 minutes. Cells were resuspended in lysis buffer (20 mM Tris-HCl pH 7.5, 5 mM $MgCl_2$, 50 mM KCl, 400 mM NaCl, 2 mM DTT, 1% Triton™ X-100, 100 U/ml aprotinin, 0.2 mM PMSF, 20% glycerol) and incubated on ice for 5 minutes. Lysates were centrifuged at 10,000 g for an additional 5 minutes. PKR was immunoprecipitated from 100 µg of this protein extract using anti-PKR monoclonal antibody (R&D Systems: MAB1980) in a high salt buffer (20 mM Tris-HCl pH 7.5, 50 mM KCl, 400 mM NaCl, 1 mM EDTA, 1 mM DTT, 100 U/ml aprotinin, 0.2 mM PMSF, 20% glycerol, 1% Triton™ X-100) at 4° C. on a rotating wheel for 30 minutes. 10 µL of protein A-Sepharose® beads were then added to each immunoprecipitate followed by an additional 1-hour incubation under the same conditions. Protein A-Sepharose® beads were washed 4 times in high salt buffer followed by an additional two washes in activity buffer (20 mM Tris-HCl pH 7.5, 50 mM KCl, 2 mM MgCl2, 2 mM MnCl2, 100 U/ml aprotinin, 0.1 mM PMSF, 5%, glycerol). PKR activity assay using PKR bound to protein A-Sepharose® beads was conducted by incorporating: 0.1 mM ATP, 10 µCi of [γ-32P] ATP, and increasing amounts of either pure recombinant wt PACT or DYT16 PACT (400 pG–4 ng) as the PKR activator. Reaction was incubated at 30° C. for 10 min and resolved on a 12% SDS-PAGE gel followed by phosphorimager analysis on Typhoon™ FLA7000.

Western Blot Analysis

Lymphoblasts derived from a compound heterozygous DYT16 patient containing both P222L and C213R mutations as independent alleles were cultured alongside lymphoblasts derived from a family member containing no mutations in PACT as our control cells. Cells were plated at a concentration of 300,000 cells/ml of RPMI media containing 10% fetal bovine serum and penicillin/streptomycin. To analyze cellular response to ER stress, cells were treated with 5 µg/ml of tunicamycin (Santa Cruz) over a 24-hour time course and harvested cells in RIPA (150 mM NaCl, 1.0% IGEPAL® CA-630, 0.5% sodium deoxycholate, 0.1% SDS, 50 mM Tris, pH 8.0) buffer containing a 1:100 dilution of protease inhibitor cocktail (Sigma) and phosphatase inhibitor (Sigma). Concentration of total protein extract was then determined using BCA assay and appropriate amounts of extracts were analyzed by western blot analyses using appropriate antibodies as indicated.

Co-Immunoprecipitation Assays with Endogenous Proteins

For co-Immunoprecipitation (co-IP) of endogenous proteins, DYT16 and wt lymphoblasts were seeded at a concentration of 300,000 cells/ml of RPMI complete media and treated with 50 μM of luteolin (Santa Cruz) over a 24-hour time course. Cells were harvested at indicated time points and whole cell extract was immunoprecipitated overnight at 4° C. on a rotating wheel in IP buffer (20 mM Tris-HCl pH 7.5, 150 mM NaCl, 1 mM EDTA, 1% Triton™ X-100, 20% glycerol) using anti-PKR antibody (71/10, R&D Systems) and protein A-Sepharose® beads (GE Healthcare). Immunoprecipitation was carried out using 100 ng of anti-PKR antibody and 10 μL of protein A-Sepharose® beads slurry per immunoprecipitation. Immunoprecipitates were washed 3 times in 500 μL of IP buffer followed by resuspension and boiling for 5 min in 1×Laemmle buffer (150 mM Tris-HCl pH 6.8, 5% SDS, 5% β-mercaptoethanol, 20% glycerol). Samples were resolved on 10% SDS-PAGE denaturing gel and probed with anti-PACT antibody to determine co-IP efficiency and anti-PKR antibody to determine equal amounts of PKR were immunoprecipitated in each sample. Input blots of whole cell extract without immunoprecipitation are shown to indicate equal amounts of protein in each sample.

Co-Immunoprecipitation Assays in HeLa Cells

In all cases HeLa M cells were seeded at 20% confluency in 6-well dishes 24 hours prior to co-transfecting 250 ng of each flag- and/or Myc-tagged constructs using Effectene® reagent (Qiagen). Cells were harvested 24 hours post transfection and harvested in IP buffer. Whole cell extract was then immunoprecipitated overnight at 4° C. on a rotating wheel with either flag-agarose (Sigma) or Myc-agarose beads (Thermo Scientific). Immunoprecipitates were then washed 3-5 times in IP buffer followed by resuspension and boiling for 5 minutes in 1×Laemmle buffer. Samples were then resolved on 10% SDS-PAGE denaturing gels and transferred to PVDF membranes. To evaluate PACT-PACT homodimerization and PACT-TRBP heterodimerization, flag-tagged constructs were immunoprecipitated using 15 μL of flag-agarose beads and blots were initially probed with anti-Myc antibody to detect co-IP (PACT), followed by re-probing with anti-flag antibody to detect efficiency of IP (PACT or TRBP). PACT-PACT homodimerization co-IP blots were incubated at 50° C. for 30 minutes in stripping buffer (62.5 mM Tris-HCl pH 6.8, 10% SDS, 0.75% β-mercaptoethanol) prior to re-probing with anti-flag antibody. To evaluate PACT-PKR interactions, Myc-tagged PACT constructs were co-transfected in pCDNA3.1− with a flag-tagged dominant negative PKR mutant, K296R, also in the pCDNA3.1−. The cell lysates were immunoprecipitated in 15 μL of Myc-agarose beads and resolved on 10% SDS-PAGE denaturing gels and transferred to PVDF membranes. Blots were initially probed with anti-flag antibody to detect co-IP (PKR) followed by re-probing with anti-Myc antibody to determine equal amount of IP (PACT) per sample. Input blots of whole cell lysate exempt from immunoprecipitation are shown to demonstrate equal expression of each construct prior to immunoprecipitation.

Mammalian 2-Hybrid Interaction Assays

In all cases, wt PACT, DYT16, TRBP, or PKR ORFs were subcloned into both pSG424 expression vector such that it created an in-frame fusion to a GAL4 DNA binding domain (GAL4-DBD), and pVP16AASV19N expression vector such that it maintains an in-frame fusion to the activation domain of the herpes simplex virus protein VP16 (VP16-AD). COS-1 cells were then transfected with: (i) 250 ng each of the GAL4-DBD and the VP16-AD constructs, (ii) 50 ng of pG5Luc a firefly luciferase reporter construct, and (iii) 1 ng of pRLNull plasmid (Promega®), to normalize for transfection efficiencies. Cells were then harvested 24 hours post transfection and assayed for both firefly and renilla luciferase activities using Dual Luciferase® Reporter Assay System (Promega®). Fusion proteins were assayed for interaction in all combinations.

Caspase 3/7 Activity Assays

Both wt- and patient-derived lymphoblasts were seeded at a concentration of 300,000 cells/ml of RPMI complete medium and treated with a concentration of 5 μg/ml of tunicamycin over a 24-hour time course. Samples were collected at indicated time points and mixed with equal parts Promega® Caspase-Glo® 3/7 reagent (Promega® G8090) and incubated for 45 minutes. Luciferase activity was measured and compared to cell culture medium alone and untreated cells as the negative controls. To address the effect of inhibiting PACT-PKR interaction on cell viability, wt and patient lymphoblasts were cultured as described above in 50 μM of luteolin for 24 hours followed by treatment with 5 μg/ml of tunicamycin in luteolin free media over the same 24-hour time course.

Results

DYT16 Mutations do not Affect PACT's dsRNA-Binding Activity

FIG. 1A illustrates the DYT16 mutations characterized in this example. FIG. 1B provides results of the dsRNA-binding assay. In FIG. 1B, T—total input; B—proteins bound to poly(I)poly(C)-agarose. Competition lanes (15-18): no competitor (—), competition with 100-fold molar excess of single-stranded RNA (ss) or dsRNA (ds). The mirror bands below the full-length PACT bands represent products of in vitro translation from internal methionine codons and thus are not produced in similar quantities in all translation reactions and thus are of variable intensity. Lanes 19 and 20 represent binding of firefly luciferase protein to poly(I)·poly(C)-agarose, used as a negative control to demonstrate specificity. For FIG. 1C, bands were quantified by phosphor-imaging analyses, and % bound was calculated. Error bars: S.D. from three independent experiments. The p-values were calculated using statistical analyses indicated no significant difference between % dsRNA-binding of wt and point mutants.

Figure 1C:
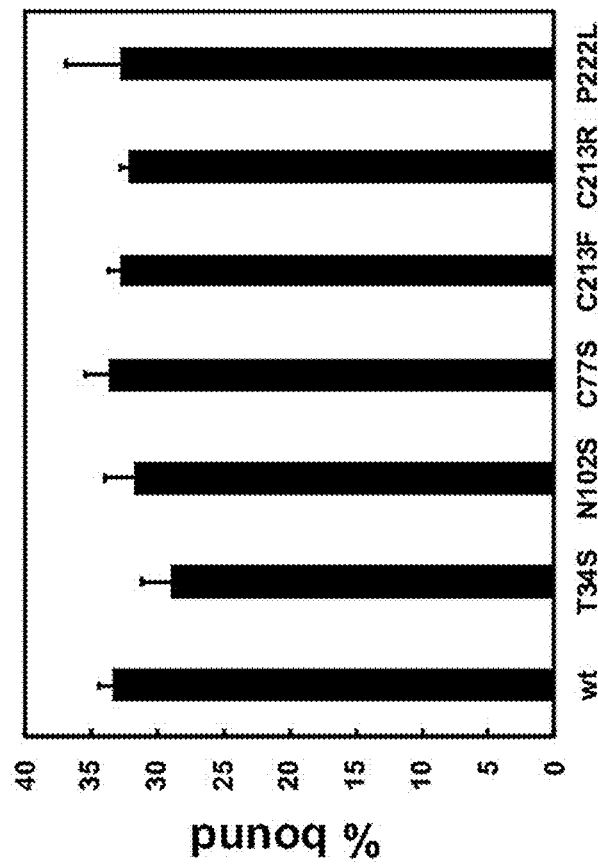
FIG. 1C provides quantification of the dsRNA binding assay of FIG. 1B.
Figure 1B:
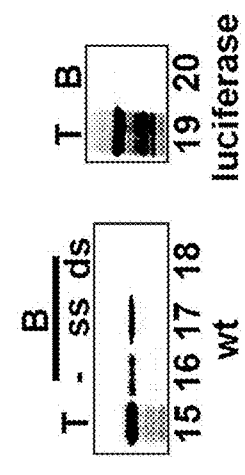
FIG. 1B provides the results of a dsRNA binding assay showing dsRNA binding activity of wild type (wt) PACT and DYT16 point mutants.

As seen in FIG. 1B and FIG. 1C, the DYT16 point mutants showed no change in dsRNA binding capabilities in comparison to the wt PACT (lanes 1-14). In order to ascertain the specificity of the dsRNA-binding assay, in vitro translated firefly luciferase, which has no dsRNA-binding activity, was used as a negative control (lanes 19-20). Additionally, the specificity of the interaction for dsRNA was demonstrated by adding excess dsRNA or ssRNA as competitors. As seen in lanes 15-18, the binding to dsRNA immobilized on beads can be effectively competed by exogenously added dsRNA but not single-stranded (ss) RNA (lanes 15-18).

DYT16 Mutants Activate PKR More Efficiently

PACT is best characterized for its ability to activate PKR under conditions of cellular stress. Therefore, the consequence of each of the DYT16 mutations was evaluated for PACT's ability to activate PKR using an in vitro PKR activity assay. Hexahistidine-tagged wt PACT ("Hexahistidine-tag" disclosed as SEQ ID NO: 11) and DYT16 mutant proteins were expressed and purified from bacterial cells using nickel affinity chromatography. The purified recombinant proteins were used as activators in an in vitro PKR activity assay by adding in increasing amounts to PKR immunoprecipitated from HeLa cells. The efficiency of PKR activation was then determined by comparing PKR autophosphorylation in the presence of wt PACT and the various PACT mutants.

Figure 2A:
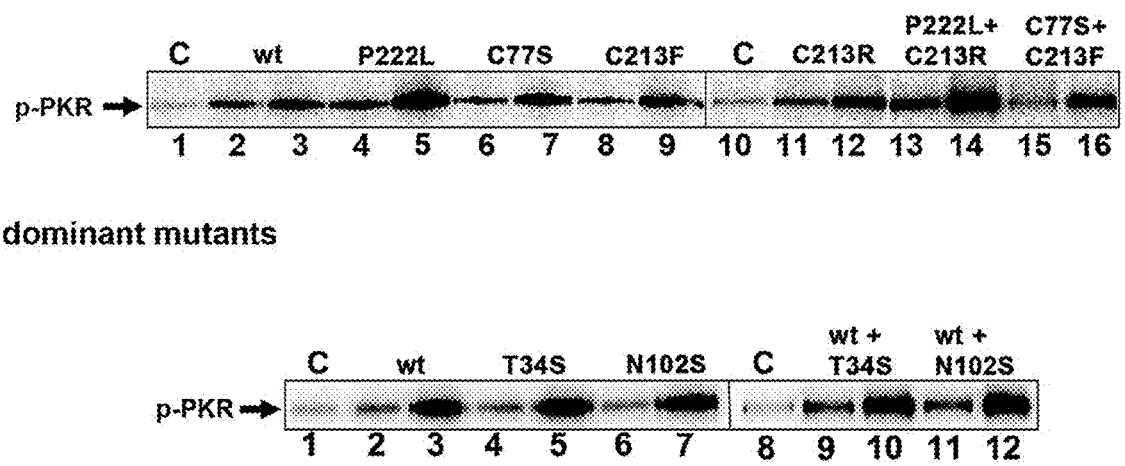
FIG. 2A provides results of a PKR kinase activity assay showing effect of DYT16 mutations.

Results are shown in FIG. 2A. In the assay, either 400 µg (FIG. 2A, lanes 2,4,6,8 top panel, and lanes 2,4,6 bottom panel) or 4 ng (FIG. 2A, lanes 3,5,7,9 top panel, and lanes 3,5,7 bottom panel) of recombinant wt PACT or DYT16 mutant proteins were used as PKR activators. Lanes 13-16 (upper panel) and Lanes 9-12 (lower panel): PACT mutants in combinations reported in DYT16 patients were used as PKR activator with 200 µg (lanes 11,13,15 top panel and lanes 9,11 bottom panel) or 2 ng (lanes 12,14,16 top panel and lanes 10,12 bottom panel) of each mutant protein.

As seen in FIG. 2A, some basal levels of activated PKR were observed in lanes 1 and 10 (upper panel) and lanes 1 and 8 (lower panel) in the absence of any added activator. When the purified recombinant PACT proteins were added, a dose dependent increase (left: 400 µg, right: 4.0 ng) in activated autophosphorylated PKR was observed (lanes 2-9, 11-16 for upper panel and lanes 2-7, 9-12 for lower panel).

Figure 2B:
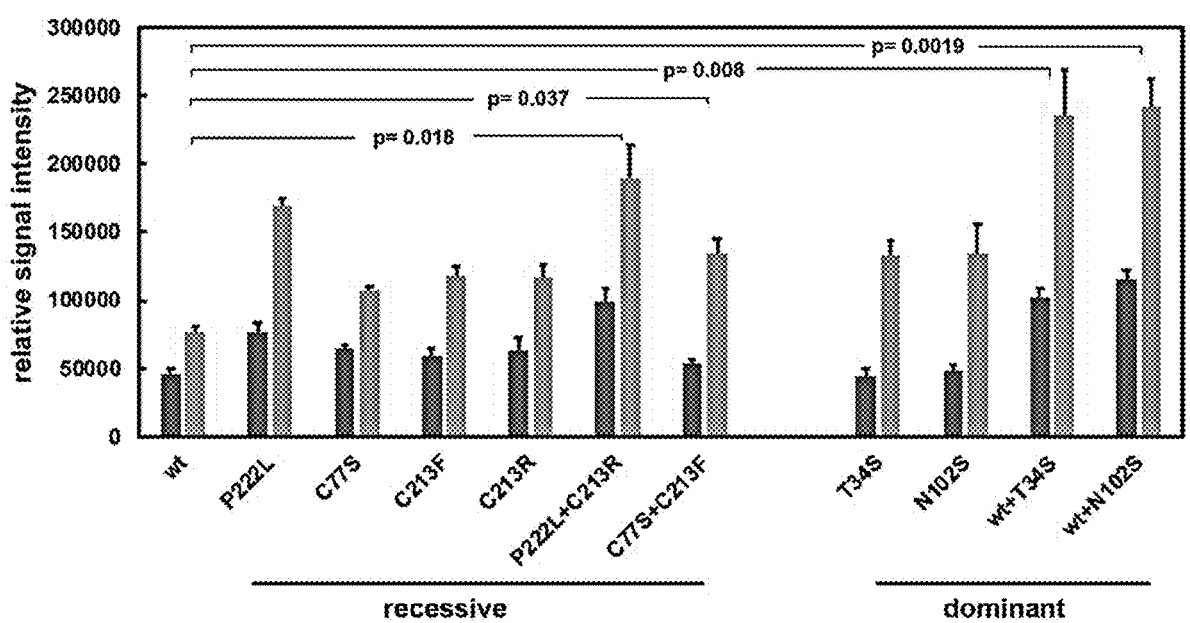
FIG. 2B provides quantification of the PKR kinase activity assay of FIG. 2A.

The amount of radioactivity present in PKR bands was quantified using a phosphorimager analysis and results are shown in FIG. 2B, in which the relative signal intensities were plotted. Dark (left) bars: PKR activity seen with 400 µg and light (right) bars: PKR activity seen with 4 ng of the corresponding pure recombinant PACT protein. In all cases, recessive mutations demonstrated a slightly increased capacity to activate PKR (FIG. 2A, lanes 4-12, and FIG. 2B) as compared to wt PACT (FIG. 2A, lanes 2-3). When tested in combinations, as reported in DYT16 patients, the recessive mutants showed significantly enhanced ability to activate PKR (FIG. 2A, upper panel lanes 13-16, and FIG. 2B). The dominant mutants (lower panel) also showed enhanced ability to activate PKR at 400 µg (FIG. 2A, lower panel lanes 4-7). When tested in combination with wt PACT, both the dominant mutants demonstrated significantly higher PKR activation (FIG. 2A, lower panel: lanes 9-12, and FIG. 2B). These results indicate that the DYT16 point mutants have enhanced ability to activate PKR as compared to wt PACT.

DYT16 Patient Derived Lymphoblasts are More Susceptible to ER Stress

Figure 2C:
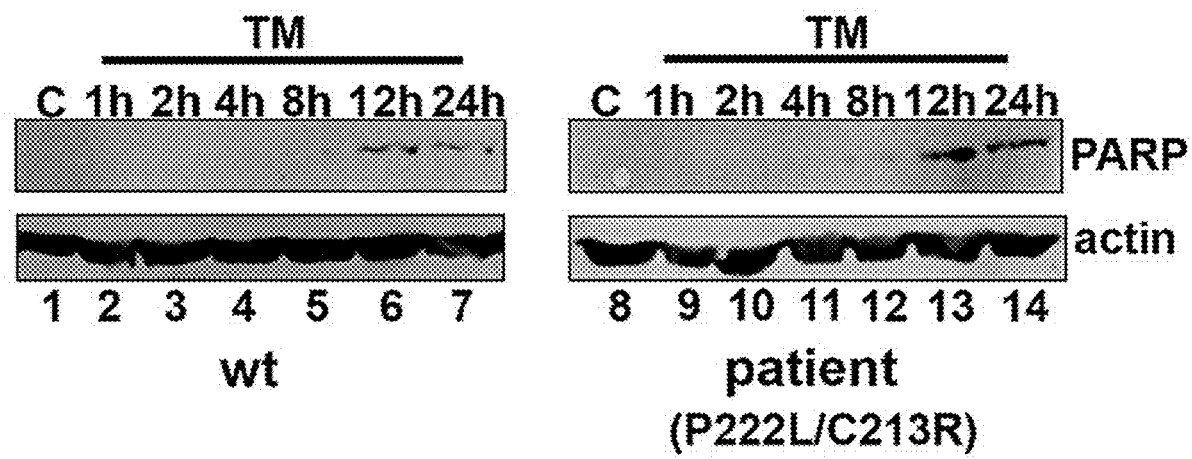
FIG. 2C provides comparison of western blot analysis of cleaved PARP1, a marker of cellular apoptosis, from whole cell extracts from wt and DYT16 subject-derived lymphoblasts.
Figure 2D:
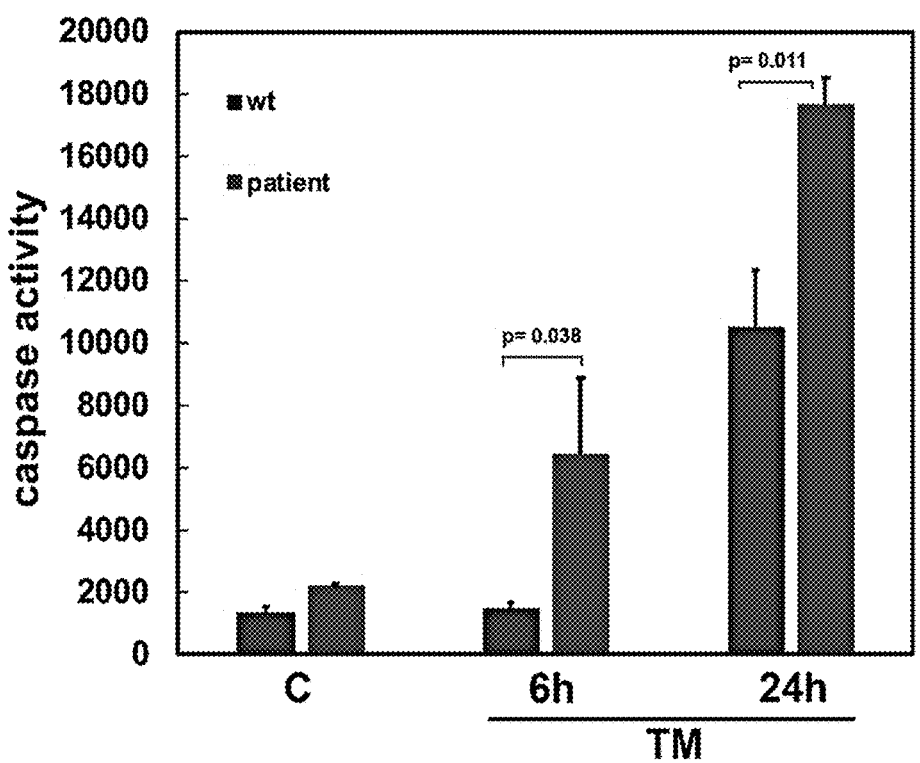
FIG. 2D provides comparison of a Caspase-Glo 3/7 activity assay from whole cell extracts from wt and DYT16 subject-derived lymphoblasts.

The lymphoblast lines derived from a DYT16 patient and his normal, wt parent were used to determine the effect of one particular DYT16 mutation combination on cell viability in response to stress. The effect of ER stress on DYT16 compound heterozygote patient-derived lymphoblast cells expressing both P222L and C213R mutations as independent alleles was characterized. These cells were compared to wt lymphoblast cell lines derived from an unaffected family member. The ER stress inducing agent, tunicamycin (TM), was utilized, which results in the accumulation of misfolded proteins in the ER due to inhibition of protein glycosylation. Results are provided in FIG. 2C and FIG. 2D. FIG. 2C provides Western blot analysis for cleaved PARP1. Specifically, whole cell extracts from the normal (wt) and DYT16 patient derived lymphoblasts treated with 5 µg/ml of tunicamycin (TM) were analyzed at indicated time points using anti-cleaved PARP1, a marker of cellular apoptosis, and anti-β-actin antibodies. FIG. 2D illustrates Caspase-Glo® 3/7 activity. Lymphoblast lines established from wt and DYT16 patient were treated with 5 µg/ml tunicamycin and the Caspase-Glo® 3/7 activities were measured at indicated time points. Light (left) bars: wt cells, and dark (right) bars: DYT16 cells. The data is an average of three independent experiments and the p values are as indicated.

In the case of wt lymphoblasts, over a 24-hour time course in response to TM treatment a marginal increase in expression of cleaved PARP1 was observed (FIG. 2C lanes 2-7). In contrast to this, in the DYT16 patient derived lymphoblasts, there was a dramatically significant increase in cleaved PARP1 in response to tunicamycin (FIG. 2C, lanes 13-14). To further validate these results, Caspase-Glo® 3/7 activity assays were performed under the same conditions to measure apoptosis. In wt lymphoblasts caspase activity was detect at 24 hours but not at 6 hours post-treatment (FIG. 2D, light (left) bars). In contrast, the DYT16 patient lymphoblasts demonstrate significantly elevated caspase activity at 6 hours which further increases at 24 hours post-treatment (FIG. 2D, dark (right) bars). This further supports that the DYT16 patient lymphoblasts are significantly more susceptible to ER stress and exhibit increased apoptosis as compared to wt cells possibly due to a failure to restore homeostasis.

eIF2α Phosphorylation and ISR is Dysregulated in DYT16 Patient Lymphoblasts

In order to elucidate the underlying mechanism driving heightened sensitivity to ER stress in DYT16 lymphoblasts, western blot analysis was performed on cells treated with TM under the same conditions probing for markers of cellular stress response. Results are shown in FIG. 3A and FIG. 3B.

Figure 3A:
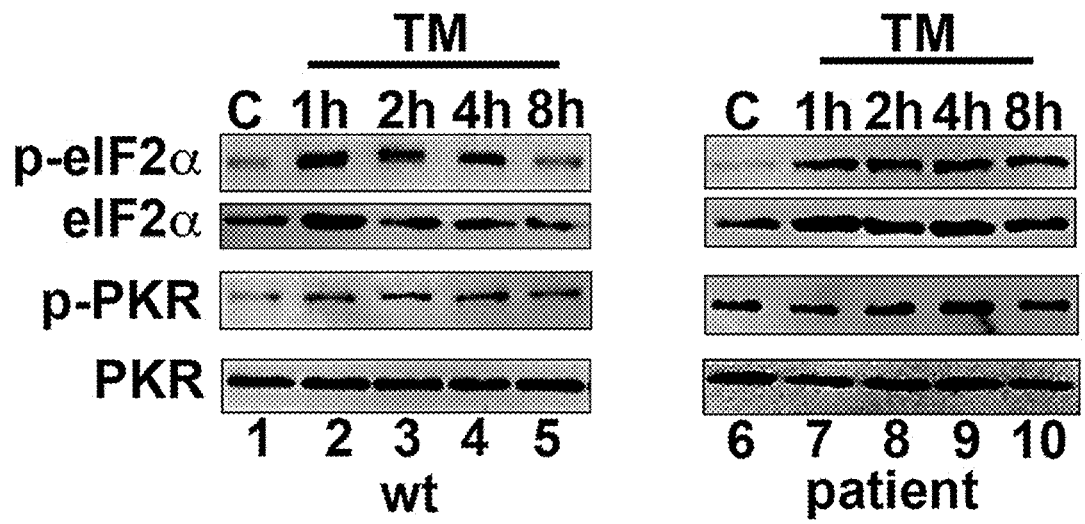
FIG. 3A provides comparison of western blot analysis for p-PKR and p-eIF2α from whole cell extracts from wt and DYT16 subject-derived lymphocytes treated with tunicamycin.
Figure 3B:
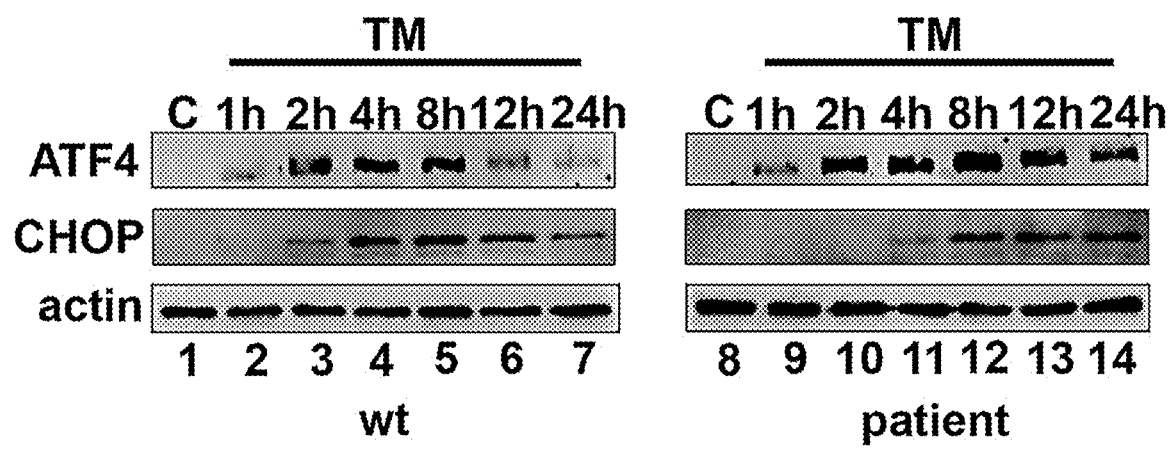
FIG. 3B provides comparison of western blot analysis for ATF4 and CHOP from whole cell extracts from wt and DYT16 subject-derived lymphocytes treated with tunicamycin.

FIG. 3A provides western blot analysis for p-PKR and p-eIF2α. Whole cell extracts from normal (wt) and DYT16 patient-derived lymphoblasts treated with 5 µg/ml of tunicamycin (TM) were analyzed at indicated time points. Blots were probed for p-eIF2α, total eIF2α, p-PKR, and total PKR. Best of four representative blots are shown.

The kinetics of both eIF2α phosphorylation and PKR activation in the DYT16 lymphoblasts were compared to the wt lymphoblasts from the unaffected family member. In wt lymphoblasts (left), a low basal level of eIF2α phosphorylation was observed in the untreated cells (FIG. 3A, lane 1) followed by increased eIF2α phosphorylation at 1-4 hours post treatment (lanes 2-4) and then restoration to basal levels by 8 hours (lane 5). In contrast to this, in the DYT16 lymphoblasts (right), a similar increase in eIF2α phosphorylation 1 hour after treatment (lane 7) was observed; however, the eIF2α phosphorylation was sustained even at 8 hours post treatment (lanes 8-10).

The time course of PKR activation in DYT16 patient lymphoblasts was studied under the same conditions. In wt lymphoblasts (left), PKR activation at 1 hour after TM treatment was observed that was sustained until 4 hours (lanes 1-4) and showed a slight decrease by 8 hours (FIG. 3A). In contrast to this, the DYT16 lymphoblasts (right) exhibited a dramatically elevated level of activated PKR even in untreated cells (lane 6) that did not show any stress-dependent increase after treatment with TM (lanes 7-10).

Due to the differences in eIF2α and PKR phosphorylation responses between wt and DYT16 lymphoblasts, the downstream effects of eIF2α phosphorylation were also examined for similar differences. FIG. 3B provides western blot analysis for ATF4 and CHOP. Whole cell extracts from normal (wt) and DYT16 patient-derived lymphoblasts treated the same as in 3A were analyzed at indicated time points. Blots were probed for ATF4, and CHOP. Best of four representative blots are shown. β-actin was used as a loading control to ensure equal amounts of protein were loaded in each lane.

In wt lymphoblasts (left), ATF4 was undetectable in untreated cells (FIG. 3B, lane 1) and its expression increases in a time dependent manner from 1 to 8 hours post treatment (lanes 2-5) and declines at 12 and 24 hours after treatment (lanes 6-7). In contrast, in the DYT16 patient lymphoblasts (right), although increased expression of ATF4 from 1 to 8 hours post treatment (lanes 9-11) was observed, it persisted at high levels even at 12 hours post treatment and showed only a small decline at 24 hours after treatment.

Levels of CHOP, an ATF4-induced proapoptotic protein, in response to TM treatment in wt and DYT16 lymphoblasts was also compared. CHOP is undetectable in untreated cells (FIG. 3B, lane 1) and its expression increased in a time dependent manner from 2 to 8 hours post treatment (lanes 3-5) and declined at 12 and 24 hours after treatment (lanes 6-7). In contrast, in the DYT16 patient lymphoblasts (right), a delay in expression of CHOP was observed and it was not detected until 4 hours post treatment (lane), and it persisted at high levels at 8-24 hours post treatment (lanes 12-14). Collectively, these results demonstrate a dysregulation of ISR pathway, prolonged phosphorylation of eIF2α, elevated levels of activated PKR, prolonged elevated levels of ATF4 translation, and delayed but sustained induction of CHOP in the DYT16 lymphoblasts.

Effect of DYT16 Mutations on PACT-PKR Interactions

Co-immunoprecipitation (co-IP) assays were performed using cells expressing a combination of Myc-epitope tagged wt or DYT16 mutant PACT and flag-epitope tagged PKR. PKR is expressed at low basal levels in cells and both increased PKR activation and increased PKR expression levels are toxic to cells as it induces apoptosis. Thus, in order to evaluate PACT-PKR heterodimer formation an expression vector encoding flag-tagged K296R, a catalytically inactive PKR mutant, was utilized which inactivates PKR's catalytic activity without affecting PACT-PKR or any other interactions. Previously, the recessively inherited DYT16 mutation, P222L, has been shown to increase ability to form PACT-PKR heterodimers relative to wt. Results obtained herein for other mutations are shown in FIG. 4A-FIG. 4D.

Figure 4A:
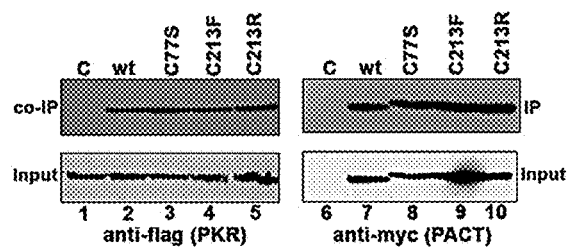
FIG. 4A provides co-immunoprecipitation results showing the effect of recessive DYT16 mutations on PACT-PKR interactions.
Figure 4B:
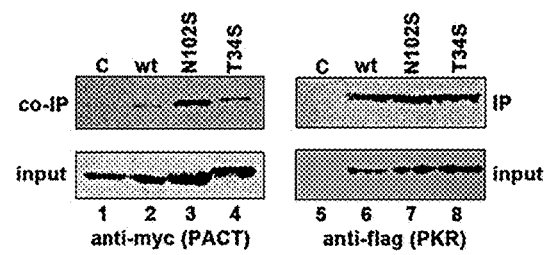
FIG. 4B provides co-immunoprecipitation results showing the effect of dominant DYT16 mutations on PACT-PKR interactions.

Specifically, FIGS. 4A and 4B provide results of co-immunoprecipitation studies in which HeLa cells were co-transfected with flag-PKR and Myc-PACT expression plasmids in pCDNA3.1—as described above. 24 hours post-transfection, cells were harvested and Myc-PACT (FIG. 4A) or flag-PKR (B) was immunoprecipitated using Myc-agarose or flag agarose beads. The immunoprecipitates were analyzed by western blot analysis with anti-flag (FIG. 4A) or anti-Myc (FIG. 4B) antibodies (co-IP panel) and with anti-Myc (FIG. 4A) or anti-flag (B) for IP panels. Input gels show expression levels of proteins without immunoprecipitation.

Figure 4C:
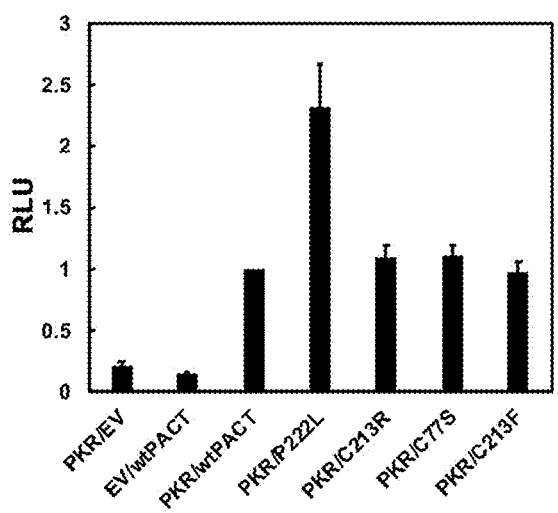
FIG. 4C provides results of a mammalian two-hybrid assay showing the effect of recessive DYT16 mutations on PACT-PKR interactions.
Figure 4D:
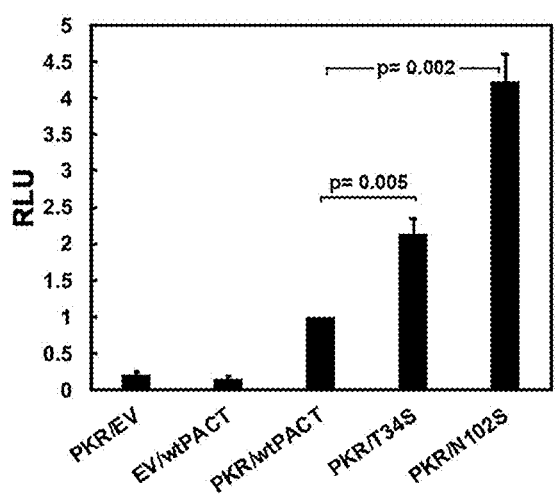
FIG. 4D provides results of a mammalian two-hybrid assay showing the effect of dominant DYT16 mutations on PACT-PKR interactions.

FIG. 4C and FIG. 4D provide results of mammalian two-hybrid assays in which HeLa cells were transfected with 250 ng of each of the two test plasm ids encoding proteins to be tested for interaction, 50 ng of the reporter plasmid pG5Luc, and 1 ng of plasmid pRL-Null to normalize transfection efficiency. Cells were harvested 24 hours after transfection, and cell extracts were assayed for luciferase activity. The plasmid combinations are as indicated, PKR was expressed as a GAL4 DNA-binding domain fusion protein (bait) and all PACT proteins were expressed as VP16-activation domain fusion proteins (preys). The experiment was repeated twice with each sample in triplicate, and the averages with standard error bars are presented. The p values are as indicated for samples with significant differences in interaction. (RLU, relative luciferase units).

Results indicate that the recessively inherited mutations (C77S, C213F, and C213R) showed no difference in their ability to interact with PKR relative to wt PACT (FIG. 4A, lanes 2-5). In the absence of Myc-PACT, no flag-PKR was immunoprecipitated confirming that there is no non-specific binding of flag-PKR to the beads in the absence of Myc-PACT (co-IP panel, lane 1). Lanes 7-10 demonstrate equal amounts of Myc-PACT proteins were immunoprecipitated in each lane (top panel) while input gels (lower panel) demonstrate equal expression of each Myc-PACT expression construct (lanes 7-10) and flag-PKR (lanes 1-5).

In contrast, an increase in the PACT-PKR heterodimer formation in case of dominantly inherited mutations (N102S and T34S) under the same conditions was observed (FIG. 4B). As compared to wt PACT (lane 2), co-IP of the dominant mutants N102S and T34S (lanes 3-4) is significantly increased. No co-IP of Myc-PACT was seen in the absence of flag-PKR (lane 1), thus demonstrating that there is no non-specific interaction of PACT proteins with the beads in the absence of flag-PKR. Lanes 6-8 (upper IP panel) demonstrate equal amounts of flag-PKR was immunoprecipitated in each lane, while input panels demonstrate equal expression of all constructs (lower panel, lanes 1-4, and 6-8).

In order to validate the co-IP results, the PACT-PKR interactions were tested using the mammalian two-hybrid (M2H) assay. In agreement with co-IP data, results demonstrated that the recessively inherited mutations C77S, C213F and C213R have no difference in their ability to interact with PKR (FIG. 4C). Consistent with previously reported data, the P222L mutant demonstrated a stronger binding to PKR as indicated by greater induction of the luciferase reporter gene compared to wt PACT (FIG. 4C). In the case of the P222L mutation, about 2.5-fold increase in the PKR interaction as compared to wt PACT was observed, whereas the other recessive mutants showed similar PKR interaction as the wt PACT. Similarly, results from the co-IP data were confirmed in case of the dominant mutations (FIG. 4D). The T34S mutant showed about 2.25-fold increase and the N102S mutant showed about 4.25-fold increase in PKR interaction relative to wt PACT (FIG. 4D).

Effect of DYT16 Mutations on PACT-PACT Interactions

Using the same protein/protein interaction studies outlined above, PACT-PACT interactions were examined for affect by the DYT16 mutations. Results are shown in FIG. 5A-FIG. 5E.

Figure 5A:
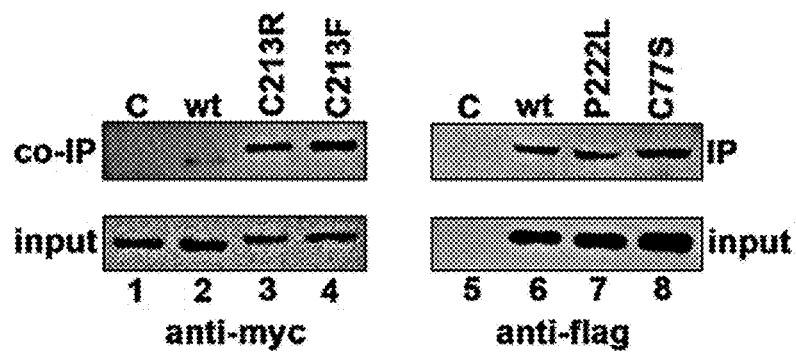
FIG. 5A provides co-immunoprecipitation results showing the effect of recessive DYT16 mutations on PACT-PACT interactions.
Figure 5B:
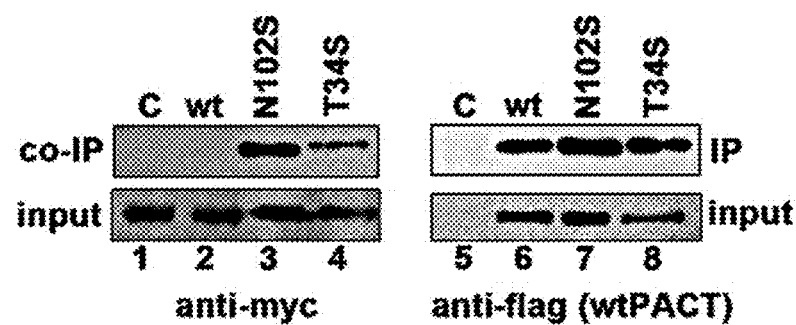
FIG. 5B provides co-immunoprecipitation results showing the effect of dominant DYT16 mutations on PACT-PACT interactions in which dominant mutants were interacted with wt.
Figure 5C:
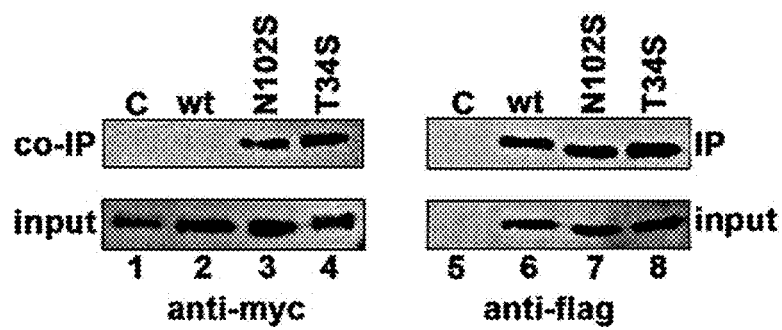
FIG. 5C provides co-immunoprecipitation results showing the effect of recessive DYT16 mutations on PACT-PACT interactions.

Co-immunoprecipitation assays were carried out to measure PACT-PACT interaction with mutant protein combinations as present in DYT16 patients. HeLa cells were co-transfected with flag-PACT and Myc-PACT expression plasmids in pCDNA3.1–. 24 hours post-transfection, cells were harvested, and flag-PACT was immunoprecipitated with flag-agarose beads. The immunoprecipitates were analyzed by western blot analysis with anti-Myc antibodies (co-IP panel) or anti-flag antibodies (IP panel). Input gels show expression levels of proteins without immunoprecipitation. FIG. 5A provides results for recessive DYT16 mutants, FIG. 5B provides results for dominant DYT16 mutant interactions with wt PACT, and FIG. 5C provides results for dominant DYT16 mutant interactions with dominant mutants (homomeric interactions). Input gels showed expression levels of proteins without immunoprecipitation.

As shown in FIG. 5A, FIG. 5B, and FIG. 5C, all DYT16 mutants showed a dramatic increase in their ability to form PACT-PACT homodimers in the absence of stress as compared to wt PACT. Minimal wt PACT homodimerization was observed (FIG. 5A, lane 2) with this being variable and no interaction being detected in few experimental repeats as it is established that in the absence of stress, PACT-PACT dimerization is usually absent. The recessively inherited DYT16 mutations showed enhanced C77S-C213F and P222L-C213R interactions as compared to wt PACT-wt PACT interactions (compare lanes 3-4 to lane 2). In the dominantly inherited mutations, ability to form wt PACT-mutant dimers was tested (FIG. 5B), as well as mutant-mutant dimers (FIG. 5C). No wt PACT homodimerization was observed in the absence of stress (FIG. 5B and FIG. 5C, lane 2); however, both the dominant DYT16 mutants N102S and T34S showed enhanced interaction with wt PACT (FIG. 5B, lanes 3-4) with N102S showing the strongest interaction with wt PACT. When evaluating these dominant mutations for their ability to interact with themselves, very strong interaction was observed between N102S-N102S and T34S-T34S (FIG. 5C, lanes 3-4) as compared to wt PACT-wt PACT with the strongest interaction being T34S-T34S. No co-IP of Myc-tagged wt PACT was observed in the absence of flag-tagged wt PACT (lane 1) demonstrating the absence of any non-specific binding to the beads (FIG. 5A-FIG. C). The IP panels show that equal amounts of flag-tagged PACT protein were immunoprecipitated in each lane (FIG. 5A-FIG. 5C, upper panels, lanes 5-8), and input blots indicate equal expression of each construct (FIG. 5A-FIG. 5C, lower panels, lanes 1-8).

Figure 5E:
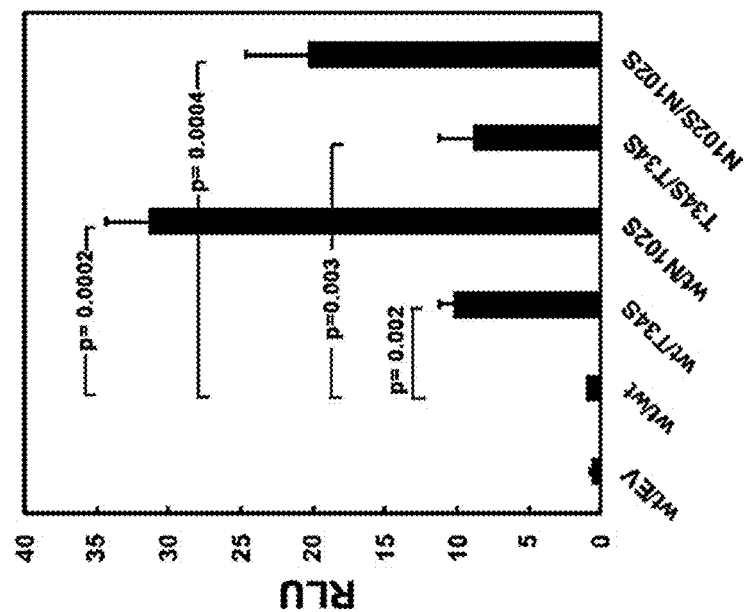
FIG. 5E provides luciferase activity of cells following transfection with luciferase reporter plasmid and various mutant PACT plasmid combinations to examine the interactions between DYT16 PACT mutants vs. wild types.
Figure 5D:
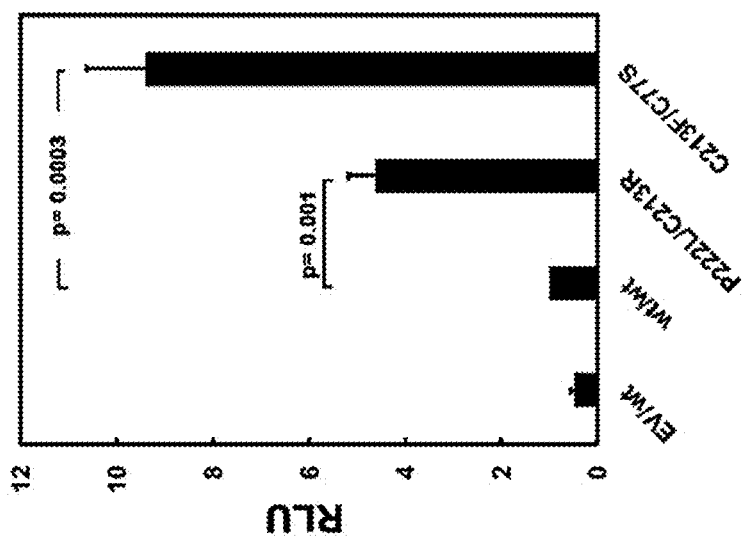
FIG. 5D provides luciferase activity of cells following transfection with luciferase reporter plasmid and various mutant PACT plasmid combinations to examine the interactions between DYT16 PACT mutants vs. wild types.

To further confirm the co-IP data, the interaction between DYT16 PACT mutants was tested utilizing the M2H. HeLa cells were transfected with 250 ng of each of the two test plasm ids encoding proteins to be tested for interaction, 50 ng of the reporter plasmid pG5Luc, and 1 ng of plasmid pRL-Null to normalize transfection efficiency. Cells were harvested 24 hours after transfection, and cell extracts were assayed for luciferase activity. The plasmid combinations are as indicated in FIG. 5D and FIG. 5E. Various PACT proteins were expressed as a GAL4 DNA-binding domain fusion proteins (bait) and also as VP16-activation domain fusion proteins (preys). The experiment was repeated twice with each sample in triplicate, and the averages with standard error bars are presented. The p values are as indicated. RLU, relative luciferase units.

As seen in FIG. 5D and FIG. 5E, in the patient specific combinations all the recessive mutants showed enhanced interactions relative to wt PACT-wt PACT interaction (FIG. 5D). The P222L-C213R and C213F-C77S interactions are ~5-fold and ~9-fold higher than wt PACT-wt PACT interaction respectively (FIG. 5D). Furthermore, the dominant mutants T34S and N102S also show enhanced interactions (FIG. 5E). The wt PACT-T34S and N102Swt PACT interactions are ~10-fold and ~30-fold higher than wt PACT wt PACT interactions. The T34S-T34S and N102-N102S interactions were enhanced ~10-fold and ~20-fold respectively compared to wt PACT-wt PACT interactions. These results further strengthen the co-IP data that the DYT16 mutations enhance PACT's ability for forming PKR activating homomeric interactions.

PACT's Ability to Interact with TRBP is not Affected by the DYT16 Mutations

The consequence of the DYT16 mutations under study on PACT-TRBP heterodimer formation were determined. Results are provided in FIG. 6A-FIG. 6D.

HeLa cells were co-transfected with flag-TRBP and Myc-PACT expression plasmids in pCDNA3.1–. 24 hours post-transfection, cells were harvested and flag-TRBP was immunoprecipitated with flag-agarose beads. The immunoprecipitates were analyzed by western blot analysis with anti-Myc antibodies (co-IP panel) and anti-flag antibody (IP panel). Input gels show expression levels of proteins without immunoprecipitation.

FIG. 6A presents results for recessive DYT16 mutants and FIG. 6B presents results for dominant DYT16 mutants. Results indicate that the recessively inherited mutations, C77S, C213F, and C213R (FIG. 6A, lanes 2-5), as well as the dominantly inherited N102S and T34S mutations (FIG. 6B, lanes 2-4), have similar binding affinity to TRBP relative to wt PACT. As the presence of Myc-wt PACT was not detected in the absence of flag-TRBP expression (lane 1, FIG. 6A and FIG. 6B) any nonspecific binding of Myc-PACT to the beads was ruled out. IP blots indicating that equal amount of Myc-TRBP protein was immunoprecipitated (FIG. 6A and FIG. 6B, IP panels, lanes 7-10 and lanes 6-8) and input blots demonstrating equal protein expression were shown (FIG. 6A and FIG. 6B, input panels, lanes 1-10 and lanes 1-8).

These results were validated using the M2H to determine the relative strengths of PACT-TRBP interactions. HeLa cells were transfected with 250 ng of each of the two test plasm ids encoding proteins to be tested for interaction, 50 ng of the reporter plasmid pG5Luc, and 1 ng of plasmid pRL-Null to normalize transfection efficiency. Cells were harvested 24 hours after transfection, and cell extracts were assayed for luciferase activity. The plasmid combinations are as indicated, TRBP protein was expressed as a GAL4 DNA-binding domain fusion protein (bait) and various PACT proteins as VP16-activation domain fusion proteins (preys). The experiment was repeated twice with each sample in triplicate, and the averages with standard error bars are presented. RLU, relative light units. The p values are as indicated; n.s. indicates not significant.

Consistent with previously reported data, the P222L mutation showed ~2-fold increase in interaction with TRBP relative to wt PACT (FIG. 6C). The other recessively inherited mutations, however, showed no difference in their ability to interact with TRBP relative to wt PACT (FIG. 6C). Consistent with the co-IP data, no difference in the PACT-TRBP interaction was observed for the dominantly inherited mutations relative to wt PACT (FIG. 6D). These results confirmed that the DYT16 mutations examined do not change PACT's interactions with TRBP.

DYT16 Patient Lymphoblasts Show Stronger PACT-PKR Interactions and its Disruption Rescues their Higher Sensitivity to ER Stress DYT16 subject-derived lymphoblasts and wt lymphoblasts derived from an unaffected family member were treated with luteolin. Results are shown in FIG. 7A and FIG. 7B.

Lymphoblasts from unaffected family member (wt) or DYT16 subject (patient) were treated with 50 µM luteolin. The cell extracts were prepared at the indicated times, and endogenous PKR protein was immunoprecipitated using anti-PKR mAb and protein A-Sepharose®, which immunoprecipitates total PKR. The immunoprecipitates were analyzed by western blot analysis with anti-PACT monoclonal antibody (Co-IP panel; FIG. 7A). The blot was stripped and re-probed with anti-PKR mAb to ascertain an equal amount of PKR was immunoprecipitated in each lane (IP panel). Input blot: Western blot analysis of total proteins in the extract with anti-PACT and anti-PKR mAbs showing equal amount of PACT and PKR in all samples.

Figure 7A:
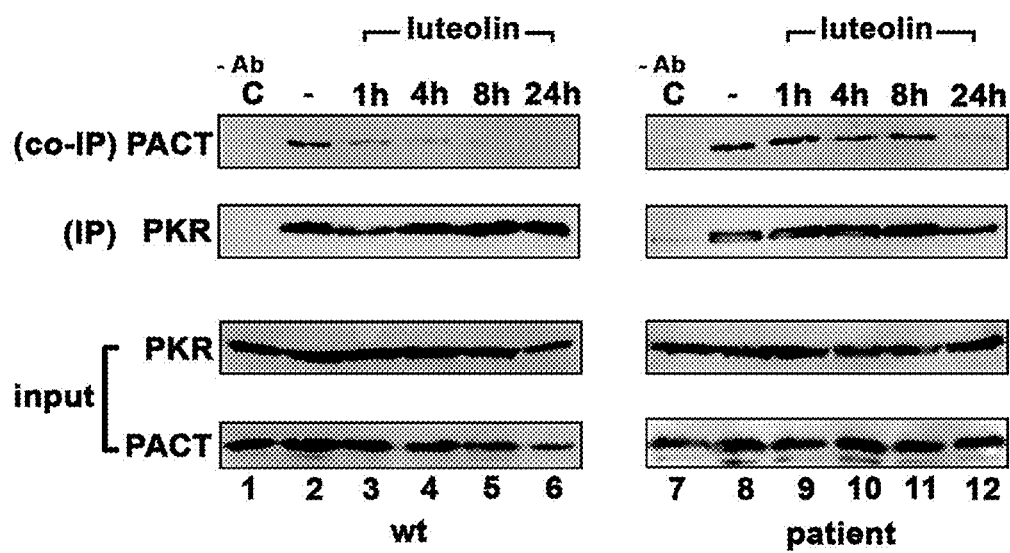
FIG. 7A provides co-immunoprecipitation results showing the effect of luteolin on endogenous PACT-PKR interactions.
Figure 7B:
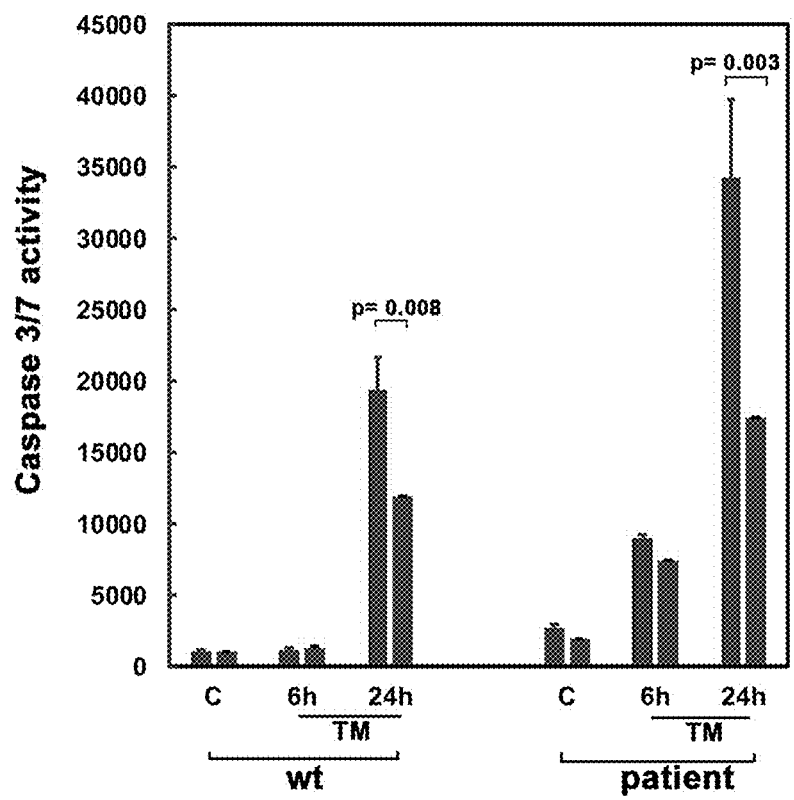
FIG. 7B presents effects of luteolin on Caspase 3/7 activity in wt and DYT16 subject-derived lymphoblasts.

As seen in FIG. 7A, in the wt lymphoblasts (left) some PACT-PKR interaction (upper panel) was detected prior to luteolin treatment (lane 2), and at 1 hour after luteolin treatment, PACT-PKR interactions were barely detectable (lane 3) and a further time-dependent decrease in the PACT-PKR interaction was seen from 1 to 8 hours (lanes 3-5), with the interaction no longer be detected at 24 hours post-treatment (lane 6). In the DYT16 patient lymphoblasts (right), much higher PACT-PKR interaction was observed prior to luteolin treatment (lane 8) and the interaction persisted until 2 hours (lanes 9-10) then decreased slowly at 4 hours and 8 hours after luteolin treatment (lanes 11-12). A complete loss of PACT-PKR interactions was seen at 24 hours after treatment in the DYT16 patient lymphoblasts (lane 12). IP blots (lower panel) demonstrated that equal amounts of PKR were immunoprecipitated in all lanes (lanes 1-12), and the input blots demonstrate that equal amount of protein was present in all IP samples.

The presence of PACT or PKR in samples incubated overnight in the absence of PKR antibody was not detected, thus demonstrating that there was no nonspecific binding of PKR or PACT to the beads in the absence of PKR antibody (lanes 1 and 7). These results confirm that PACT-PKR interaction is stronger in DYT16 patient cells as compared to the wt cells and that a 24-hour treatment with luteolin disrupts the interaction in wt as well as DYT16 cells.

The data indicates that there is an increase in both PACT-PACT (FIG. 5A-FIG. 5E) and PACT-PKR interactions (FIG. 4A-FIG. 4D and FIG. 7A) in DYT16 patient-derived lymphoblasts, and the DYT16 patient lymphoblasts are more susceptible to ER stress induced apoptosis (FIG. 2D). Therefore, it was next determined if disrupting the PACT-PKR interaction in the DYT16 patient lymphoblasts would lead to an increase in cell viability in response to ER stress. As a 24-hour treatment with luteolin of both wt control and DYT16 patient lymphoblasts could significantly disrupt PACT-PKR interactions (FIG. 7A, lanes 6 and 12), prior luteolin treatment was tested to determine if it would be protective for DYT16 patient lymphoblasts after ER stress. As seen in FIG. 7B, in the wt control lymphoblasts no Caspase-Glo® 3/7 activity was detected in the untreated samples or at 6 hours after TM treatment but there was a significant increase in caspase activity at 24 hours post treatment (FIG. 7B, light (left) bars). The cells treated for 24 hours with luteolin prior to TM treatment showed a marked reduction in Caspase-Glo® 3/7 activity (FIG. 7B, dark (right) bars). In contrast, the DYT16 patient cells show higher basal levels of Caspase-Glo® 3/7 activity prior to TM treatment that was enhanced at 6 hours post-treatment and a further increase is seen at 24 hours (FIG. 7B, light (left) bars). This increase was dramatically reduced, especially at 24 hours post treatment, when cells were treated with luteolin 24 hours prior to TM treatment (FIG. 7B, dark (right) bars). These results demonstrate that disrupting PACT-PKR interactions with luteolin in DYT16 cells can protect the cells from ER stress-induced apoptosis.

While certain embodiments of the disclosed subject matter have been described using specific terms, such description is for illustrative purposes only, and it is to be understood that changes and variations may be made without departing from the spirit or scope of the subject matter.

SEQUENCE LISTING

```
Sequence total quantity: 11
SEQ ID NO: 1           moltype = DNA  length = 35
FEATURE                Location/Qualifiers
source                 1..35
                       mol_type = other DNA
                       organism = synthetic construct
SEQUENCE: 1
gctctagaca tatggaaatg tcccagagca ggcac                               35

SEQ ID NO: 2           moltype = DNA  length = 70
FEATURE                Location/Qualifiers
source                 1..70
                       mol_type = other DNA
                       organism = synthetic construct
SEQUENCE: 2
gcctctgcag ctctatgttt cgccagcttc ttacttgtac cttcacctgt ggaggttatg    60
tcaccaacgg                                                          70

SEQ ID NO: 3           moltype = DNA  length = 35
FEATURE                Location/Qualifiers
source                 1..35
                       mol_type = other DNA
                       organism = synthetic construct
SEQUENCE: 3
gctctagaca tatggaaatg tcccagagca ggcac                               35

SEQ ID NO: 4           moltype = DNA  length = 44
FEATURE                Location/Qualifiers
source                 1..44
                       mol_type = other DNA
                       organism = synthetic construct
SEQUENCE: 4
ggagaattcc tcaaggaatg ccaagtaaat cctaaagaat gtcc                     44

SEQ ID NO: 5           moltype = DNA  length = 35
FEATURE                Location/Qualifiers
source                 1..35
                       mol_type = other DNA
                       organism = synthetic construct
SEQUENCE: 5
gctctagaca tatggaaatg tcccagagca ggcac                               35
```

```
SEQ ID NO: 6           moltype = DNA  length = 44
FEATURE                Location/Qualifiers
source                 1..44
                       mol_type = other DNA
                       organism = synthetic construct
SEQUENCE: 6
ggagaattcc tcaaggaatg ccaagtacgt cctaaagaat gtcc                  44

SEQ ID NO: 7           moltype = DNA  length = 53
FEATURE                Location/Qualifiers
source                 1..53
                       mol_type = other DNA
                       organism = synthetic construct
SEQUENCE: 7
gctgcagagg ctgccataaa cattttgaaa gccagtgcaa gtatttgctt tgc         53

SEQ ID NO: 8           moltype = DNA  length = 30
FEATURE                Location/Qualifiers
source                 1..30
                       mol_type = other DNA
                       organism = synthetic construct
SEQUENCE: 8
ggggatcctt actttctttc tgctattatc                                  30

SEQ ID NO: 9           moltype = DNA  length = 35
FEATURE                Location/Qualifiers
source                 1..35
                       mol_type = other DNA
                       organism = synthetic construct
SEQUENCE: 9
gctctagaca tatggaaatg tcccagagca ggcac                            35

SEQ ID NO: 10          moltype = DNA  length = 37
FEATURE                Location/Qualifiers
source                 1..37
                       mol_type = other DNA
                       organism = synthetic construct
SEQUENCE: 10
cgtgtaatac ctgaatcggt gatttccctg gcttagc                          37

SEQ ID NO: 11          moltype = AA  length = 6
FEATURE                Location/Qualifiers
source                 1..6
                       mol_type = protein
                       organism = synthetic construct
SEQUENCE: 11
HHHHHH                                                             6
```

What is claimed is:

1. A method for disrupting PACT-mediated PKR activation in a cell, comprising:
   administering luteolin the cell; wherein,
   the cell exhibits a dysregulation in PACT-mediated PKR activation; and wherein,
   following the administration, an interaction between PACT protein expressed by the cell and PKR protein expressed by the cell is decreased as compared to the interaction prior to the administration.

2. The method of claim 1, further comprising determining a concentration or rate of formation of a PACT-PKR heterodimer prior to and following the administration, wherein the interaction decrease is indicated by a decrease in the PACT-PKR heterodimer concentration or rate of formation following the administration.

3. The method of claim 1, further comprising determining a concentration or rate of formation of a PACT-PACT homodimer prior to and following the administration, wherein the interaction decrease is indicated by a decrease in PACT-PACT homodimer concentration or rate of formation following the administration.

4. The method of claim 1, further comprising determining a concentration or rate of formation of a PACT-TBRP heterodimer prior to and following the administration, wherein the interaction decrease is indicated by an increase in PACT-TBRP heterodimer concentration or rate of formation following the administration.

5. The method of claim 1, wherein the PACT protein expressed by the cell comprises a mutation.

6. The method of claim 5, wherein the mutation comprises one or more of a cysteine to serine mutation, a cysteine to phenylalanine mutation, a cysteine to arginine mutation, a proline to leucine mutation, threonine to serine mutation, and an asparagine to serine mutation.

7. The method of claim 5, wherein the mutation comprises one or more of T34S, N102S, C77S, C213F, C213R, and P222L.

8. The method of claim 1, wherein the luteolin is administered to the cell such that the luteolin contacts the cell at a concentration of from about 10 μM to about 100 μM.

9. A method for decreasing an abnormal integrated stress response in a cell, the method comprising:
   determining a first expression or activity level of a stress biomarker expressed in response to the abnormal stress response;
   following the determination, administering luteolin the cell; and following the administration, determining a second expression or activity level of the stress biomarker; wherein the second expression or activity level is within about 10% of a normal, non-stress expression or activity level for the biomarker in the cell.

10. The method of claim 9, wherein the cell expresses a mutated PACT protein.

11. The method of claim 10, wherein the mutation comprises one or more of a cysteine to serine mutation, a cysteine to phenylalanine mutation, a cysteine to arginine mutation, a proline to leucine mutation, threonine to serine mutation, and an asparagine to serine mutation.

12. The method of claim 9, wherein the biomarker comprises an endoplasmic reticulum stress biomarker.

13. The method of claim 12, wherein the endoplasmic reticulum stress biomarker comprises accumulation of misfolded proteins in an endoplasmic reticulum of the cell, anti-cleaved PARP1 antibody, anti-β-actin antibody, binding immunoglobulin protein, phosphorylated Inositol Requiring 1 protein, phosphorylated PKR-like ER kinase, C/EBP homologous protein.

14. The method of claim 9, wherein the biomarker comprises an oxidative stress biomarker.

15. A method for treating a dysregulation in PACT-mediated PKR activation in a subject, the method comprising administering to the subject a composition comprising a therapeutically effective amount of luteolin.

16. The method of claim 15, wherein the subject has been diagnosed with a dystonia.

17. The method of claim 16, wherein the dystonia is a congenital dystonia or an induced dystonia.

18. The method of claim 16, wherein the dystonia is dystonia 16.

19. The method of claim 15, wherein the subject has been diagnosed with Alzheimer's disease, Parkinson's disease, Huntington's disease, dementia, prion disease, or Down's Syndrome.

* * * * *